US008554577B2

(12) United States Patent
Joe et al.

(10) Patent No.: US 8,554,577 B2
(45) Date of Patent: Oct. 8, 2013

(54) ELECTRONIC MEDICAL RECORDS INFORMATION SYSTEM

(76) Inventors: Ronald Stephen Joe, Vancouver (CA); Antoni Grzegorz Otto, Vancouver (CA)

(*) Notice: Subject to any disclaimer, the term of this patent is extended or adjusted under 35 U.S.C. 154(b) by 598 days.

(21) Appl. No.: 11/951,249

(22) Filed: Dec. 5, 2007

(65) Prior Publication Data

US 2009/0150289 A1 Jun. 11, 2009

(51) Int. Cl.
*A61B 5/00* (2006.01)
*G06F 19/00* (2011.01)

(52) U.S. Cl.
USPC ............................................................ 705/3

(58) Field of Classification Search
USPC ............................................................ 705/2, 3
See application file for complete search history.

(56) References Cited

U.S. PATENT DOCUMENTS

| | | | |
|---|---|---|---|
| 6,339,767 B1* | 1/2002 | Rivette et al. ................ | 707/2 |
| 6,807,543 B2 | 10/2004 | Muthya | |
| 6,978,268 B2 | 12/2005 | Thomas et al. | |
| 2002/0186818 A1* | 12/2002 | Arnaud et al. ............... | 378/165 |
| 2003/0046307 A1* | 3/2003 | Rivette et al. ............... | 707/104.1 |
| 2003/0069758 A1 | 4/2003 | Anderson et al. | |
| 2003/0154208 A1* | 8/2003 | Maimon et al. .............. | 707/100 |
| 2004/0153465 A1 | 8/2004 | Singleton et al. | |
| 2004/0267762 A1* | 12/2004 | Tunning et al. .............. | 707/100 |
| 2005/0075906 A1* | 4/2005 | Kaindl et al. ................ | 705/2 |
| 2005/0086235 A1* | 4/2005 | Jhingan ....................... | 707/100 |
| 2005/0114405 A1 | 5/2005 | Lo | |
| 2005/0149575 A1 | 7/2005 | Baune | |
| 2005/0234740 A1* | 10/2005 | Krishnan et al. ............. | 705/2 |
| 2006/0053128 A1 | 3/2006 | Gestrelius et al. | |
| 2006/0206502 A1 | 9/2006 | Gaurav et al. | |
| 2006/0259519 A1 | 11/2006 | Yakushev et al. | |
| 2007/0061266 A1 | 3/2007 | Moore et al. | |
| 2007/0061393 A1* | 3/2007 | Moore ......................... | 709/201 |
| 2007/0271316 A1* | 11/2007 | Hollebeek ................... | 707/204 |

FOREIGN PATENT DOCUMENTS

WO PCT/US01/27522 3/2002

OTHER PUBLICATIONS

Beckley, D.A., Empirical comparison of associative file structures, Foundations of Data Organization. Proceedings of the International Conference, 1985, 315-9.
Andrews, R.D., A common data structure for complex clinical data, MUMPS: A World Class Technology. MUMPS Users' Group Meeting, 1990, Orlando, FL, USA.
Steil, H. et al., EuCliD(R)—a medical registry, 4th International Workshop on Biosignal Interpretation (BSI 2002), Jun. 24-26, 2002, Como, Italy.
Quan, W. et al, The "EP Manager": a database Management Sytem for Electrophysiology Practice, North Shore University Hospital-Cornell University Medical College, NY 1994 USA.
U.S. Appl. No. 09/947,141, filed Mar. 7, 2002, Chen et al.

* cited by examiner

*Primary Examiner* — John Pauls
*Assistant Examiner* — Trang Nguyen
(74) *Attorney, Agent, or Firm* — Cameron IP

(57) ABSTRACT

There is provided an apparatus for organizing a clinical observation in the form of clinical information entered by a user into memory. The apparatus includes a mechanism to receive the clinical information, which is associated with the clinical observation and has a plurality of clinical attributes. There is a mechanism for parsing the clinical information, and which identifies a clinical information data structure representative of the clinical information and which has one or more granule information data structures. Each of the granule information data structures has a collection of generic attributes. There is a mechanism to assign the clinical attributes to respective ones of the generic attributes of the one or more granule information data structures. The clinical information data structure associates the clinical attributes with respective ones of the generic attributes of each of the granule information data structures.

3 Claims, 11 Drawing Sheets

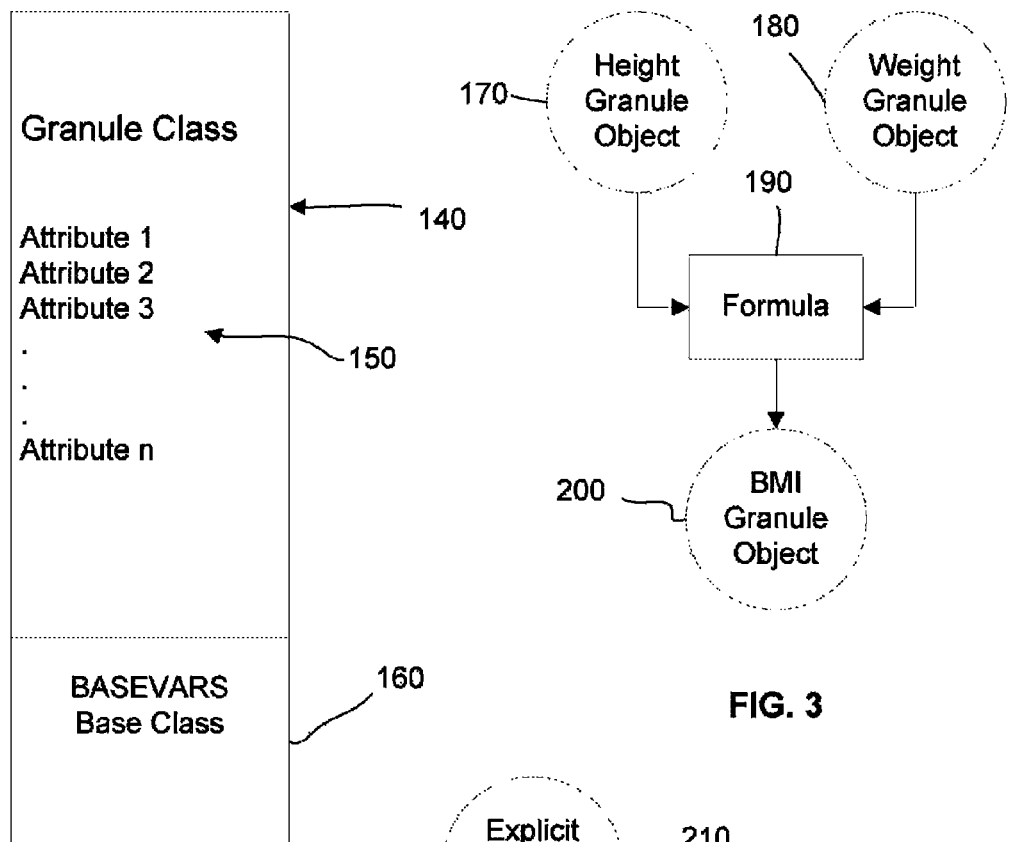
FIG. 2
FIG. 3
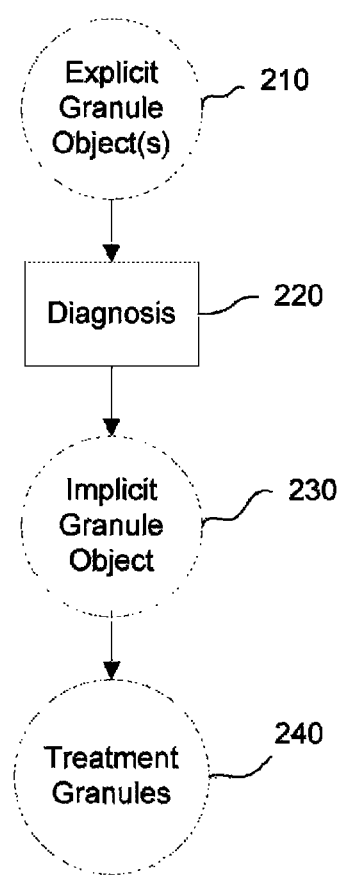
FIG. 4

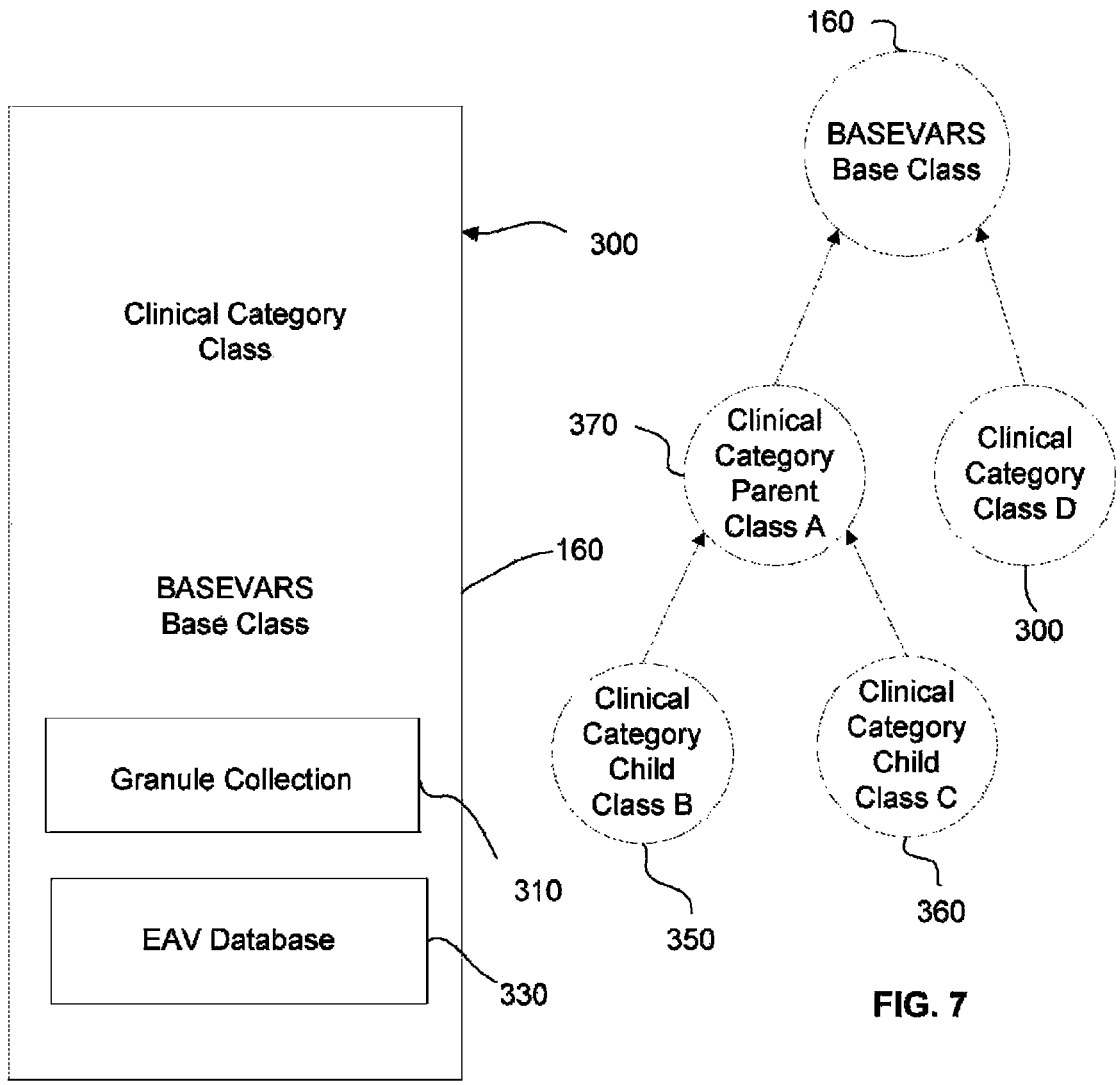
FIG. 5
FIG. 7
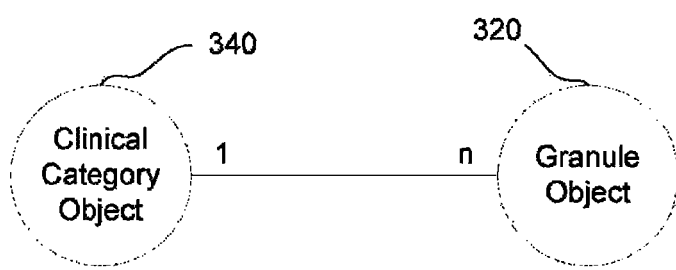
FIG. 6

```
Public Name As String
Public Type As String
Public _OwnerSegment As String
Public _OwnerGUID As System.Guid
Public KeyWord As String
Public Context As String
Public Code As Object
Public ClinicalCategory As String
Public SubjectRelationship As String
Public BodySide As String
Public FindingSite As String
Public Morphology As String
Public BodyAP As String
Public BodyAxis As String
Public BodyPosture As String
Public BodyPhysiology As String
Public Emphasis As String
Public Onset As String
Public Severity As String
Public Qualifier As String
Public procedureContext As String
Public AssociatedProcedure As String
Public Symptom As String
Public Substance As String
Public CausitiveAgent As String
Public CodeDescription As String
Public Certainty As String
Public Temporal As String
Public DateCertainty As String
Public Conditional As Object
Public TimeSpan As TimeSpan
Public Verb As String
Public Comment As String
Public IsExplicit As Boolean
Public Is Implicit As Boolean
Public IsNewFinding As Boolean
Public IsSource As Boolean
Public IsSummary As Boolean
Public IsSummaryFromSource
Public Sources As ArrayList
Public IsConditional As Boolean
Public IsClientSubjective As Boolean Public IsClientDelegateSubjective As
Public IsDiagnosis As Boolean
Public IsNegativeFinding As Boolean
Public IsPositiveFinding As Boolean
Public IsPast As Boolean
Public IsPresent As Boolean
Public IsFuture As Boolean
Public IsResolved As Boolean
Public DateResolved As Date
Public DateResolvedCertainty As String
Public IsHeld As Boolean
Public IsPendingSubmission As Boolean
Public IsSubmitted As Boolean
Public IsReported As Boolean
Public IsExamination As Boolean
Public IsTestOrder As Boolean
Public IsLabOrder As Boolean
Public IsRadiologyOrder As Boolean
Public IsPrescriptionOrder As Boolean
Public OrderType As String
Public IsReferral As Boolean
Public IsDerived As Boolean
Public IsDerivedFrom As ArrayList
Public IsCopy As Boolean
Public IsCopyOf As System.Guid
Public IsResult As Boolean
Public IsPendingResult As Boolean
Public IsAbnormal As Boolean
Public IsAbnormalFlags As String
Public IsNormal As Boolean
Public DateSubmitted As Date
Public GUID As System.Guid
Public GUIDParent As System.Guid
Public Text As String
Public IsStringWithDate As Boolean
Public IsDynamicRender As Boolean
Public Parent As Object
Public Children As ArrayList
Public Value As Object
Public Units As String
Public Note As Object
Public Terminator As String
```

FIG. 20

ELECTRONIC MEDICAL RECORDS INFORMATION SYSTEM

BACKGROUND OF THE INVENTION

1. Field of the Invention

The present invention relates generally to the field of electronic medical records, and more particularly to an information system for the storage, handling, processing, versioning, auditing and security of electronic medical records.

2. Description of the Related Art

An electronic medical record (EMR) is a term used to describe patient health information contained in a record for use by a physician at a doctor's office. Correspondingly, an electronic patient record (EPR) describes patient health information intended for use by the patient; and an electronic health record (EHR) describes patient health information used in a hospital setting. Each of these terms is used interchangeably around the world, e.g. an EMR in Canada corresponds to an EPR in England. The present invention is designed to work with any of these record types.

The International Statistical Classification of Diseases and Related Health Problems, or ICD, attempts to classify diseases and has created codes for a wide variety of signs, symptoms, abnormal findings, complaints, social circumstances, and external causes of injury or disease. Every health condition can be assigned a unique category and given a code, up to six characters long. Categories include sets of similar diseases.

For example, using ICD-9 coding, a diabetic is coded as 250. What this means is that when care providers communicate, "250" is understood as "diabetes". Finer granularity is achieved by adding an extra digit, e.g. "2501" is understood as 'Diabetes with coma'. ICD is an example of a "two-attribute granule". That is, the code "250" and the description "Diabetes".

Unfortunately, this is inadequate for EMR information systems for a number of reasons. First, one can find the code to describe a disease only about 50% of the time because either the correct code cannot be found easily or because a code does not exist for that condition. Second, there are no additional attributes to describe the condition further. In the diabetic example, other information such as the date of diagnosis, severity, or whether there is any family history etc. cannot be described within the above schema.

Systematized Nomenclature of Medicine, or SNOMED, is a systematically organized collection of medical terminology covering most areas of clinical information such as diseases, findings, procedures, micro-organisms, pharmaceuticals etc. It allows a standardized way of indexing, storing, retrieving, and aggregating clinical data so they can be accessed and understood by disparate medical information systems. It also helps to organize the content of medical records, and to reduce the variability in the way data is captured, encoded and used for clinical care of patients and research.

While SNOMED does a good job of defining concepts, their relationships, and primitive qualifiers in addition to providing a larger number of medical terms than ICD (370,000 versus 10,000), it falls short in clinical encoding as the number of attributes used to describe the encoded concept limits it. This limitation requires SNOMED to create a new concept and code for every exception that does not have an adequate qualifier to describe it.

Conventional EMR information systems comprise a relational database that includes a complicated assortment of interrelated tables, e.g. such systems can have between 500 to 4000 tables. It is well known that in order to add a column of information to the database it will cost upwards of $1 million, due to the complexity of the interrelations between the tables.

Over the years a mountain of medical information has been collected in EMR information systems. There is an advantage in data mining this information in order to aid diagnosis and treatment of a patient's condition, and for statistical analysis on the medical health of the population as a whole.

Complex and time consuming search queries are required in conventional EMR information systems since this mountain of data is distributed over 500 to 4000 relational database tables. This has inhibited the discovery of medical correlations due to the sheer complexity in locating pertinent information, and has lead to the limited access to this information by health professionals and researchers due to the time consuming nature in performing queries on such complicated data storage systems.

Conventional EMR information systems are static in nature with regard to the information they store. This limitation is related to the fixed nature of the relational database structure used. For example, patient demographic information has conventionally included the name of the patient, and their home address. As can be imagined, this information quite often changes throughout the life of the patient. The previous name and address information is quite often discarded when the new name and address are included in the EMR of the patient, and at the very least the previous historical information becomes inaccessible through the EMR information system.

This is problematic since quite often historical medical information may be associated with the name of the patient, and removing the history of the patient's name may result in losing part of the medical history of the patient. There is a great disadvantage in conventional EMR information systems in not keeping a complete history of a patient's EMR, and in not being able to view the state of a patient's EMR at a particular point in time.

There is a need for an improved EMR information system that eliminates the complexity of conventional EMR information system relational database structures. Such an improved EMR information system would facilitate data mining activities in a simple and timely manner, as well as provide a mechanism to record and playback the complete history of a patient's EMR. In addition, such a new improved EMR information system would include a universal encoding methodology for the recordation of medical observations.

BRIEF SUMMARY OF INVENTION

In one aspect of the present invention there is provided a memory for storing data for access by an application program that is executed on a data processing system. The memory includes a data structure that includes information resident in a database used by the application program. The data structure includes a clinical information data structure that has a clinical observation associated therewith. The clinical observation includes a plurality of clinical attributes. The clinical information data structure includes one or more granule information data structures. Each of the granule information data structures has a collection of generic attributes. The clinical attributes of the clinical observation mapping to the generic attributes of the one or more granule information data structures.

In another aspect of the present invention there is provided an apparatus for organizing a clinical observation in the form of clinical information entered by a user into memory. The apparatus includes a mechanism for receiving the clinical information entered by the user. The clinical information is associated with the clinical observation and has a plurality of clinical attributes. There is a mechanism for parsing the clinical information entered by the user and a mechanism for identifying a clinical information data structure representative of the clinical information entered by the user. The clinical information data structure is associated with the clinical observation and has one or more granule information data structures. Each of the granule information data structures has a collection of generic attributes. The apparatus further includes a mechanism for assigning the clinical attributes of the clinical information to respective ones of the generic attributes of the one or more granule information data structures. The clinical information data structure associates the clinical attributes of the clinical information with respective ones of the generic attributes of each of the granule information data structures.

In another aspect of the present invention there is provided an apparatus for versioning clinical information in an electronic medical records information system. The apparatus includes mechanisms for retrieving existing clinical information from a first location in a memory store and for presenting the existing clinical information to a user. There is a mechanism for receiving a signal from the user to version the existing clinical information. The apparatus also includes a mechanism for copying the existing clinical information as a version to a second location in the memory store. The second location in the memory store contains one or more versions of the clinical information.

In another aspect of the present invention there is provided an apparatus for visually playing back versioned information to a user in a graphical user interface. The apparatus includes a mechanism for displaying a version of the versioned information to a user in the graphical user interface. There is a mechanism for selecting a different version of the versioned information including a slider control. The slider control is displayed in the graphical user interface. The user adjusts the slider control thereby providing a version selection signal. The apparatus also includes a mechanism for retrieving the different version of the versioned information. The mechanism for retrieving receives the version selection signal and retrieves the different version. The mechanism for displaying displays the different version.

In another aspect of the present invention there is provided an apparatus for clinical contextual encounter between a patient and a clinician in an electronic medical records information system. The apparatus includes a mechanism to receive new clinical information related to the patient into the electronic medical records information system. A mechanism is provided to recognize a fundamental unit of medical observation of the new clinical information. There is also a mechanism to retrieve historical clinical information related to the patient from a memory store. The historical clinical information is of the same type of the fundamental unit of medical observation. The apparatus further includes a mechanism to present the new clinical information and the historical clinical information to the clinician, whereby a trend in the fundamental unit of medical observation is thereby displayed. The apparatus may include a mechanism to analyze the new medical information and the historical medical information and to provide an opinion or a diagnosis.

BRIEF DESCRIPTION OF DRAWINGS

The invention will be more readily understood from the following description of preferred embodiments thereof given, by way of example only, with reference to the accompanying drawings, in which:

FIG. 2 is a block diagram view of a granular class of the electronic medical records information system of FIG. 1;

FIG. 3 is a block diagram of a derived granule algorithm of the electronic medical records information system of FIG. 1;

FIG. 4 is a block diagram of an implicit granule algorithm of the electronic medical records information system of FIG. 1;

FIG. 5 is a block diagram view of a clinical category class of the electronic medical records information system of FIG. 1;

FIG. 6 is a block diagram of a relationship between a clinical category object and granule objects of the electronic medical records information system of FIG. 1;

FIG. 7 is a class diagram of clinical category classes of the electronic medical records information system of FIG. 1;

FIG. 20 is a computer listing of common generic attributes of the granule class of FIG. 2.

DESCRIPTION OF THE PREFERRED EMBODIMENTS

Figure 1A:
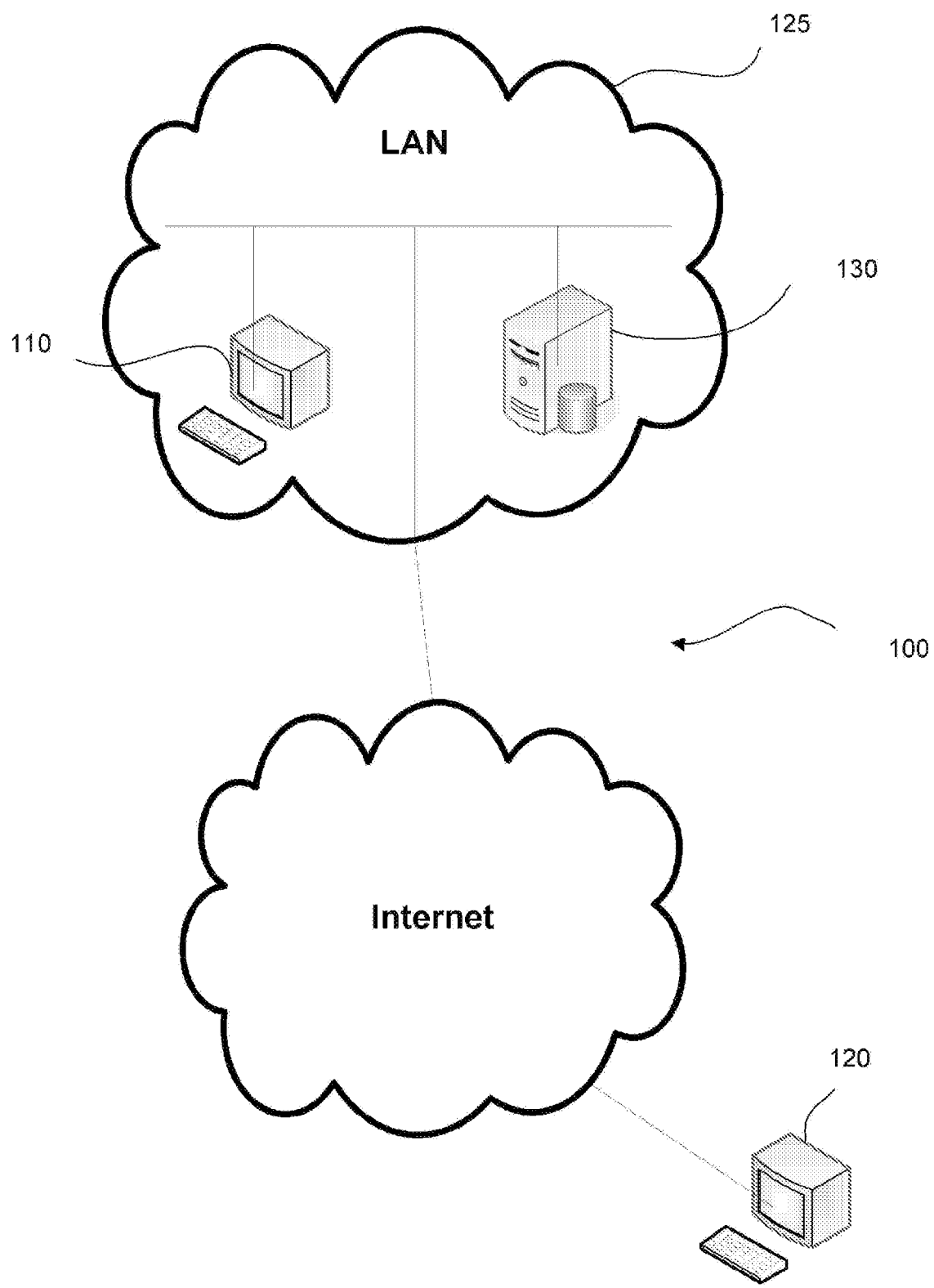
FIG. 1a is a network diagram view of an electronic medical records information system according to one embodiment of the present invention.
Figure 1B:
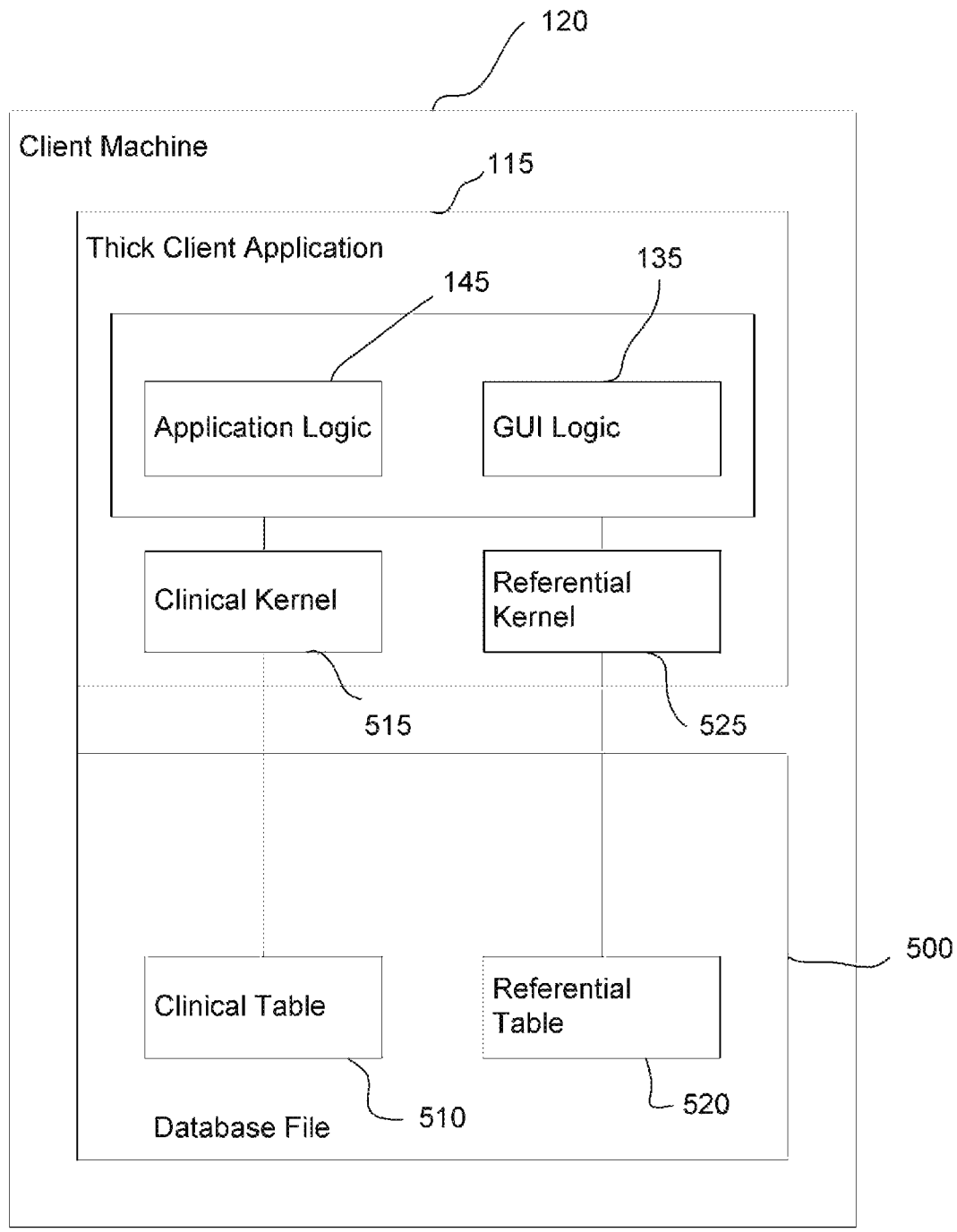
FIG. 1b is a block diagram of a thick client application architecture on a client machine of the electronic medical records information system of FIG. 1.

Referring to the figures and first to FIGS. 1a and 1b, there is an electronic medical records (EMR) information system generally indicated by reference numeral 100. The EMR information system 100 comprises software and hardware components in a distributed environment, for the storage, handling, processing, versioning and security of electronic medical records.

In a simplified environment there are client machines 110 and 120, which in the present example are personal computers, and a database server machine 130. In other embodiments there can also be an application sever. The client machine 110 and the database server 130 are collocated in a data center 125. The client machines 110 and 120 run a thick-client application 115 in the present example, but in other examples they can run a thin client web browser for communication with the application server. The client machines 110 and 120 are in communication with the database server 130 over private and public IP networks in order to exchange EMR information.

The client machines 110 and 120 present a graphical user interface 135 to a user which in combination with application logic 145 allows a user to view, modify and add EMR information. An existing EMR is retrieved from the database server 130, and any additions or modifications are sent from the client machines 110 or 120 back to the database server 130.

The present invention introduces a novel approach to the management of clinical information from clinical observation to an EMR. This includes a novel approach to recordation of a unit of medical observation, commonly called a granule. A collection of granules is collected into a larger unit called a clinical category which encapsulates clinical information and comprises one or more medical observations. The clinical category forms the basis of an EMR, and serves as the fundamental unit of storage. The EMR exposes certain key information that is descriptive of the EMR, which facilitates database queries. The EMR also encapsulates a mechanism for the versioning without loss of historical data. Each of these topics will be described in detail below.

Granule Class

Referring to FIG. 2 we now discuss the novel approach to the recordation of the fundamental unit of medical observation known as the granule. The specifics of the data structure used to store and handle the granule consists of a granule class indicated generally by reference numeral 140, which includes a collection of common generic attributes 150. The granule class 140 inherits a base class 160, which includes most of the logic that handles the basic housekeeping tasks, which will be discussed in more detail below. Most classes in the EMR information system 100 inherit the base class 160.

The granule class 140 is coding system agnostic. Any coding system may be embedded within it. One of the attributes 150 of the granule class 140 is "CODING SYSTEM" and can be assigned a value of "ICD", "SNOMED", or any other coding system. Therefore, existing coding systems can be combined with the additional capabilities of the granule class 140. In fact, a coding system is chosen to best meet the needs of the type of clinical capture. For example ICD or SNOMED may be used to capture diagnoses, Logical Observation Identifiers Names and Codes (LOINC) may be used to capture laboratory values, and locally developed billing codes may be used for billing etc. No matter what the coding system, the attributes 150 of the granule class 140 remain the same in order to reduce the variability of description and consistency of storage.

The generic attributes 150 can be extended to include new attributes. The concept of the granule class 140 is to extend the number of attributes until a saturation state is achieved, i.e. there are no more qualifiers needed to describe every possible unit of clinical observation, or clinical attributes, known to medicine. Referring to FIG. 20, there are approximately eighty-four defined attributes 150 within the granule class 140. It is expected that there will be close to two hundred attributes 150 before saturation is achieved. While not all the attributes 150 have been identified thus far, the inherent extensibility of the granule class 140 allows additions to be made as they are discovered without adversely affecting those stored in legacy systems, as will be discussed in more detail below.

Many of the attributes 150 satisfy not only a need to better define a clinical observation, but also solve existing problems in information systems. Therefore, the granule class 140 should not be considered purely clinical but informational/clinical. For example, while SNOMED is the most elaborate method developed thus far to describe clinical findings, it falls short in conveying a multitude of additional information items. In contrast, the granule class 140 is a single data type class, which is capable of containing all these additional information items and of enforcing consistency of expression of all possible clinical observations. The utilization of the granule class 140 achieves the necessary granularity and allows highly complex clinical observations to be handled in a simple and consistent way by health information systems.

Further, one of the attributes 150 is a globally unique identifier (GUID), which uniquely identifies each of the granules 140 such that no two granules are the same in any information system. The GUIDs ensure that back-ups and replications of clinical observations do not become mistaken for a number of distinct observations when they actually refer to a single observation. For example, when many health providers collaborate in patient treatment, a single lab value may be copied to several providers for their perusal. The GUID attribute of the granules class 140 ensures that copies of a single lab observation are not confused with multiple lab observations instead. Clearly, such confusion may have unintended and potentially dangerous consequences to patient care. The ISCOPY and ISCOPYOF attributes of the granule class 140 enforce this concept by explicitly noting it to be a copy of an existing granule.

The granule class 140 includes attributes for the following data items: a specific Name, a Value, Units, a Keyword, the context in which the observation was made, a coding system and its code, body specifics, a severity, an emphasis, etc., which are included in the collection of attributes 150. Depending on the clinical observation, some or all of the attributes 150 of the granule 140 may be assigned a value.

A granule may be derived from existing granules, in which case the attribute ISDERIVED is set true. For example, referring to FIG. 3, a body mass index is commonly calculated from a weight and a height. Both height and weight are separate clinical observations and reside in respective granules 170 and 180. Note that the granules 170 and 180 are instances of the granule class 140. The two granular entities 170 and 180 can be combined by way of calculation using formula 190. In the present example the calculation is based on the weight divided by the square of the height to create a new body mass index (BMI) granule 200. The BMI granule 200 is then said to be derived from the height and weight granules 170 and 180 respectively. The EMR information system 100 is designed to automatically create such derived granules by using known and accepted formulae 190.

Derivative granules are important to the future of medicine, and computing provided by automated features may be utilized in clinical decision support. The ISDERIVED BMI granule 200 includes an attribute called ISDERIVEDFROM, which is an array of references (GUIDs) to the integral granules. In the above case, therefore, the array would simply contain GUID references to the height and weight granules 170 and 180 respectively. This is one of the key features of the granule 140, which enables sharing and interoperability.

The BMI granule 200 can then be shared with other providers without transferring its integral granules, i.e. the height and weight granules 170 and 180 respectively. However, in transferring the BMI granule 200 a reference to the height and weight granules remains in the ISDERIVEDFROM array. If the provider who received the BMI granule 200 requires the actual height and weight values from which the BMI granule was derived, and if appropriate trust permissions are set up between the providers, then the source granules may be obtained by querying back without the need of the sending provider to deal with the request physically.

In providing a solution to interoperability, the specifics of the query back-trust mechanism have tremendous potential to save administrative health care dollars by avoiding the need for multiple contacts and communications between providers and/or institutions. With reference to FIG. 20, the granule class 140 has ISSUMMARY, ISNEWFINDING, and ISSUMMARYFROMSOURCE attributes, which help to avoid confusion of replicated information in an interoperable health care world.

The nature, quality, and reliability of clinical information obtained from interviews can often be incorrectly or inadequately captured due to lack of additional qualifying information. For example, qualifying information may indicate whether the information was obtained directly from the patient or relayed by other sources. Information sources are often from other providers or delegates of the patient such as family members or friends. The attributes 150 of the granule class 140 to handle these scenarios are ISCLIENTSUBJECTIVE and ISCLIENTDELEGATESUBJECTIVE. The findings may be explicitly noted to be a finding of a particular nature, i.e. ISNEGATIVEFINDING, ISPOSTIVEFINDING, ISNORMAL, ISABNORMAL and ISABNORMALFLAGS.

The granule class 140 includes a TIME or TIMESPAN attribute. The dates of historical information may be vague or approximate as indicated by the DATECERTAINTY, ISRESOLVED, and DATERESOLVED attributes, and the description may relate to time as in ISPAST, ISPRESENT, and ISFUTURE.

Referring to FIG. 4, granules may be created explicitly or implicitly. By way of example, a lab result is captured in an explicit granule 210 encapsulating a blood glucose level clinical observation. The EMR information system 100 would perform a diagnosis 220 on the explicit granule 210, and depending upon the blood glucose level could result in a diagnosis of diabetes. An implicit granule 230 is created and is flagged as ISIMPLICT rather than ISEXPLICIT.

The implicit diabetes granule 230 is created dynamically by the EMR information system 100, and is a 'diagnosis granule' containing the diabetes diagnosis. The diabetes granule 230 would then automatically and transparently trigger a series of recommendations that clinicians would need to perform in order to treat this condition in concordance with accepted treatment guidelines. The recommendations are expressed as additional treatment granules 240. The consistent way in which these varying clinical entities are stored avoids ambiguity and uncertainty that may arise when dealing with clinical categorization and lends itself to easy reuse of data and elimination of unnecessary duplication.

Various housekeeping features within all granules include attributes such as: ISHELD, ISREFERRAL, ISPENDINGSUBMISSION, ISSUBMITTED, ISREPORTED and ISRESULT, which provide a generic way of documenting granules that are action based, i.e. test orders, billings, etc. The prefix "IS" followed by a noun or phrase describing a quality, as used in the attributes above and other attributes within the granule class 140, indicates that the attribute has that quality if the attribute is assigned a logical true value.

The structure of the granule class 140 incorporates broad category clinical observations by means of the attributes 150 such as: ISEXAMINATION, ISTESTORDER, ISLABORDER, ISRADIOLOGYORDER, ISPRESCRIPTIONORDER, ORDERTYPE and ISREFERRAL.

Clinical Category Classes

Referring now to FIGS. 5, 6 & 7, a clinical category storage mechanism is discussed. Broad clinical observations are called clinical categories, and are encapsulated in the clinical category class indicated generally by reference numeral 300. The clinical category class 300 inherits the base class 160, in the present example, and includes a collection 310 of granule objects 320 and an embedded Entity-Attribute-Value (EAV) database 330. The granule objects 320 are instances of the granule class 140.

An instance of a clinical category class 300 is a clinical category object (CCO) 340 which includes one or more of the granule objects 320. Each CCO 340 represents the fundamental unit of the EMR, and comprises one or more granule objects 320, which represent the fundamental unit of medical observation. Each CCO 340 is stored within a single database row entry, as will be discussed in more detail below.

The clinical category class 300 associates, or maps, clinical attributes of one or more clinical observations to the generic attributes of respective granule objects 320. The collection 310 of all the CCOs 340 is considered to be a granular layer. The granular layer provides an efficient mechanism for running advanced queries on the database, which is discussed in more detail below.

The granules 320 are agnostic of or dissociated from the clinical attributes of the clinical observation represented by the clinical category object 340 from which they are derived. The attributes of a single granule give it the ability to describe any clinical observation that may arise, including its characteristics and the circumstances in which it was formed.

The granules 320 in turn inherit attributes of the base class 160. Therefore, the granules 320 are infinitely extensible and capable of responding to changes in medicine by their ability to alter and create clinical categories. The above structure gives the EMR information system 100 the ability to evolve as it were, without having to redesign or to re-work the framework or architecture of the application.

The base class 160 within the clinical category class 300 provides a mechanism to add new attributes to the granule class 140 without altering either the granule class 140 or the clinical category class 300. Keeping the clinical category class 300 definition relatively static also ensures that serialization into persistent storage is possible and remains consistent. Most of the attributes 150 seen in FIG. 20 are defined through the use of a Property statement of the programming language, in the present example VB.Net. The Property statement makes use of GET and SET procedures created for the attainment and assignment of values respectively. When a value is sought for any of the attributes 150 described above through the GET procedure, it calls a function in the base class 160 to find it in the embedded EAV database 330.

The EAV database 330 is necessary due to the vastness of the number of the attributes 150 in the granule class 140 of which many, as mentioned earlier, may not be known until the EMR information system 100 has been used in actual settings for some time. As the number of the attributes 150 grow, these attributes would simply be added to the EAV database 330 embedded within the base class 160.

Note that only the assigned attributes 150 through the SET command are stored in persistent storage. The GET procedure for an attribute 150 that is not assigned in the current granule object 320 simply returns a default value and does not take up persistent storage space.

The base class 160 in the clinical category class 300 provides a mechanism to store any number of granule objects 320 within the CCO 340, again without altering the class structure of the clinical category class. The granule collection 310 provides the mechanism to create new granule objects 320 as needed by the clinical category object 340.

The base class 160 provides an ability to associate with other clinical category classes 300 in a hierarchical, parent/child fashion thereby permitting this hierarchical structure in a flat file. Referring to FIG. 7, child clinical category classes 350 and 360 inherit parent clinical category class 370 which in turn inherits the base class 160; and the clinical category class 300 is shown inheriting the base class 160. The base class 160 manages the hierarchical structure and through the EAV database 330 provides a mechanism to extend a clinical category to include new variables in a dynamic fashion without changing the structure of persistent storage, or preventing legacy software from functioning.

The clinical category class 300 clusters similar smaller medical observations described within the granule objects 320 into larger, more easily manageable clinical category objects 340. Examples of clinical category classes include patient demographics, drugs, lab tests, orders, etc. New clinical category classes can be created without affecting other clinical category classes.

Figure 8:
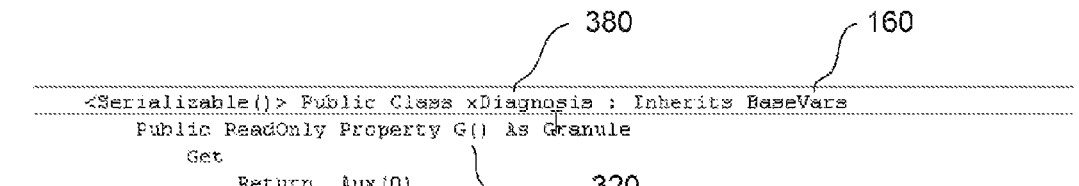
FIG. 8 is a computer listing of a diagnosis clinical category class of the electronic medical records information system of FIG. 1.

Referring to the code block in FIG. 8, a Diagnosis clinical category class 380 is defined as xDiagnosis, which, by convention, inherits the base class 160. The Diagnosis clinical category class 380 includes one granule object 320 which holds the diagnosis, returned as "G" in the programming language. The procedural call _Aux(0) is a call to retrieve the granule object 320 located at position zero in the granule collection 310.

Typically, a user will enter diagnosis information which is parsed by the application logic 145 seen in FIG. 1b. The application logic 145 then instantiates a clinical category object from the clinical category class 380 by calling the method New indicated by reference numeral 390. The New method 390 associates, or maps, the clinical attributes of the diagnosis clinical observation to the granule object 320 by assigning the clinical attributes to respective ones of the generic attributes of the granule object 320. This does not preclude this CCO from holding more than one diagnosis. Most CCO's would hold many granules.

Persistent Storage—Clinical Table

Figure 9:
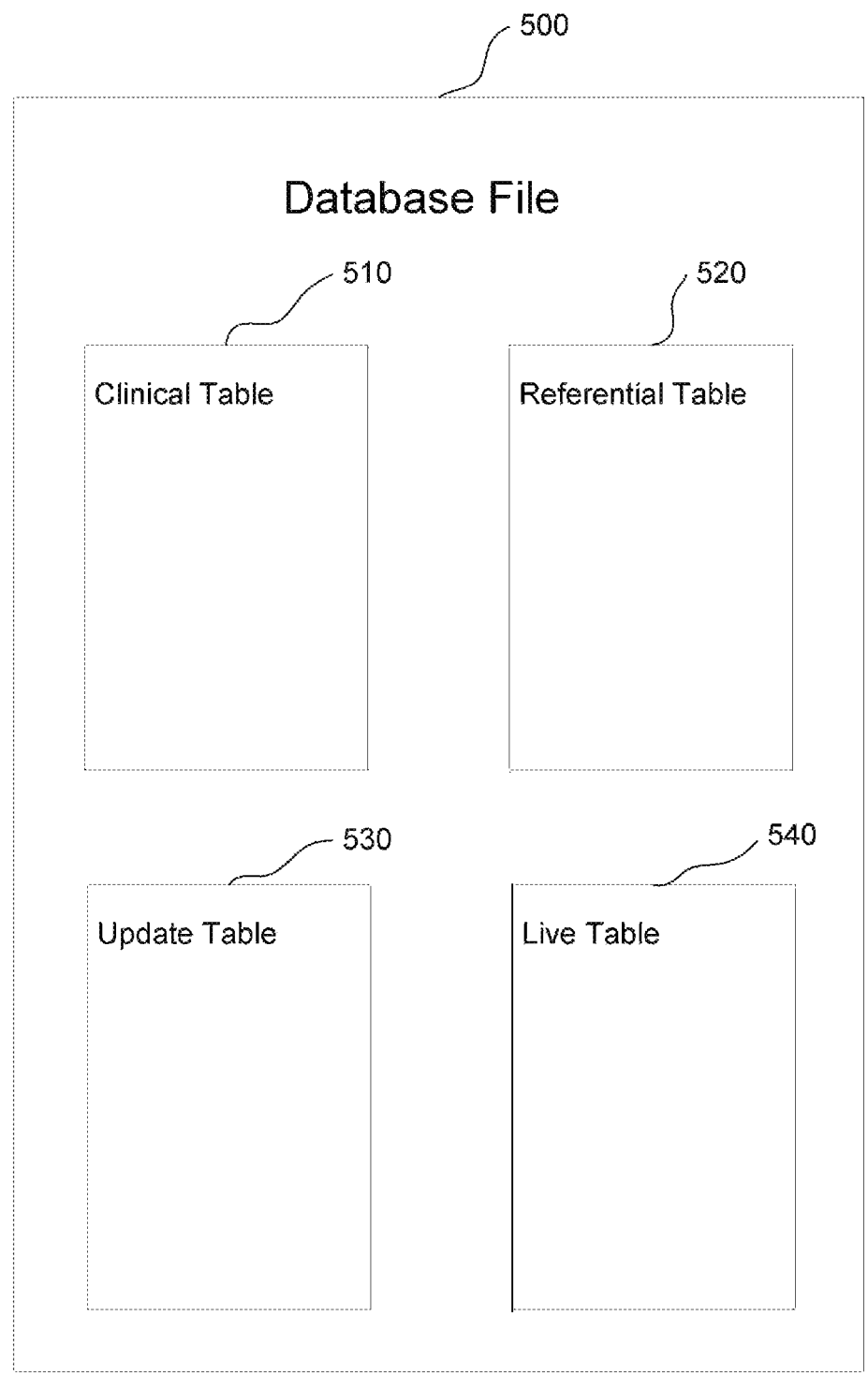
FIG. 9 is a block diagram view of a database file of the electronic medical records information system of FIG. 1.

Referring now to FIGS. 1a, 1b and 9, the persistent storage used in the EMR information system 100 is now discussed in more detail. The database server 130 includes a database in the form of a flat file 500. The flat file 500 includes clinical table 510 comprising patient information, i.e. the electronic medical records (EMRs), and referential table 520 comprising fixed information, e.g. billing and diagnostic codes.

There is also an update table 530 and a live table 540, which are used to exchange information and resolve changes made between, for example, the thick client application 115 on the client machine 120 and the data server 130 in the data center 125. This is particularly useful after the thick client application 115 has been operating in a "disconnected" or "stand alone" state.

The storage method used for clinical information does not require any cross-references to child or relational tables as typically employed in relational databases. The EMR information system 100 stores patient EMRs of an entire organization in the single clinical table 510. Clinical content includes, but is not limited to, patient demographics, problem lists, medical history, encounters, medications, lab and radiology tests results etc.

As mentioned above, the clinical category object (CCO) 340 is organized in an objected-oriented hierarchical structure providing a complex relational structure. The CCO 340, which describes an entire clinical category, is stored by serialization as a single binary field into one column of a single row of the clinical table 510 in the flat file 500. Each CCO 340 occupies its own row in the clinical table 510. Versioned data, i.e. fixed temporal copies of the CCO 340, reside in a separate binary field stored in an adjacent column of the same row. Other columns in the clinical table 150 include meta-information describing the information in the binary fields.

A patient's medical record is represented by a collection of row entries in the clinical table 510, which includes defined clinical category objects (CCO) 340, such as demographics, medical history, physical examination findings, progress notes, lab results, prescriptions etc. The patient's medical record can be built by retrieving all the CCOs 340 that are identified as belonging to a particular patient. All such CCOs 340 are identified as belonging to the particular patient by way of a patient GUID stored as another column in the clinical table 510.

The EMR information system 100 is database agnostic in the sense that it may store data within disparate database systems such as SQL, ACCESS, ORACLE, SYBASE, INTERBASE, and others. Further, the EMR information system 100 is capable of storing data in more than one database system simultaneously and in fact does so as part of its normal operations. This is achieved through the ability to store all clinical observation data in a simple manner in the clinical table 510. This feature uniquely enables the EMR information system 100 to be easily deployed on disparate systems that may utilize their own preferred databases.

Clinical categories are subject to change and new categories may need to be defined due to the constantly changing and evolving nature of medicine. New categories of clinical information can be handled without modifying the structure of the clinical table 510 or changes to the existing data therein. Recall that conventional EMR information systems employ relational table data relationships, and new clinical categories in these systems require typically both new tables and changes to existing tables.

The structure of the clinical table 510 lends itself to adapting to the ever changing needs of clinical information systems. Thus by design, the EMR information system 100 is not dependent on the peculiarities of each database management system, rather it is able to transgress multiple database management systems without fear of loss of data integrity.

In addition, no matter what content may exist in these new clinical category classes, storage and handling is done in a consistent manner by way of a direct 1:1 mapping of each of the CCOs 340 to a row in the clinical table 510. The type of the CCO 340 is identified by a column in the clinical table 510 called "Segment", which is unique for each type of CCO.

All changes made to a CCO entry in a patient's record are recorded within the same row in which the data resides, including changes to temporal and user information so that information is never deleted from a patient's record and a complete history is available at all times including additions, modifications and logical deletions. It is possible for a user to play back and roll back changes when deemed necessary. Duplication of a single row in the clinical table 510, therefore, results not only in the duplication of the current data but also duplicates the complete history of changes leading up to the current state. These are important auditing and versioning features, described in more detail below.

A security method locks down the EMRs with an encryption and compression policy to protect the sensitive clinical information. Each row of the clinical table 510 is marked with a globally unique identifier (GUID) to allow subsets of the master table to be distributed, processed and modified in a disconnected fashion. For example, a copy of the flat file 500 can be exchanged between the database server 130 and the client machines 110 and 120. Changes are resolved by performing a match to the GUID of the replicated row and analyzing the data versions encapsulated in the row.

Examples of CCO Storage

Figure 10:
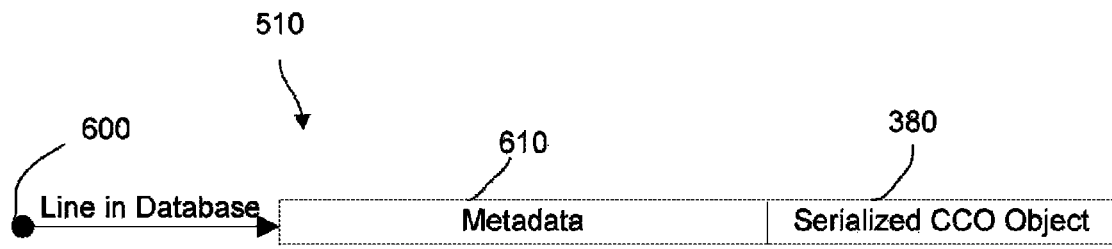
FIGS. 10, 11, 12 and 13 are block diagram views of rows in a clinical table of the database file of FIG. 9.

Referring now to FIGS. 10 to 14, examples of storing the CCOs 340 in the clinical table 510 are shown. FIG. 10 shows a simplified view of a row 600 of the clinical table 510, showing metadata 610 and the diagnosis clinical category object 380, for example. The clinical category object 380 has one granule, the granule object 320.

Figure 11:
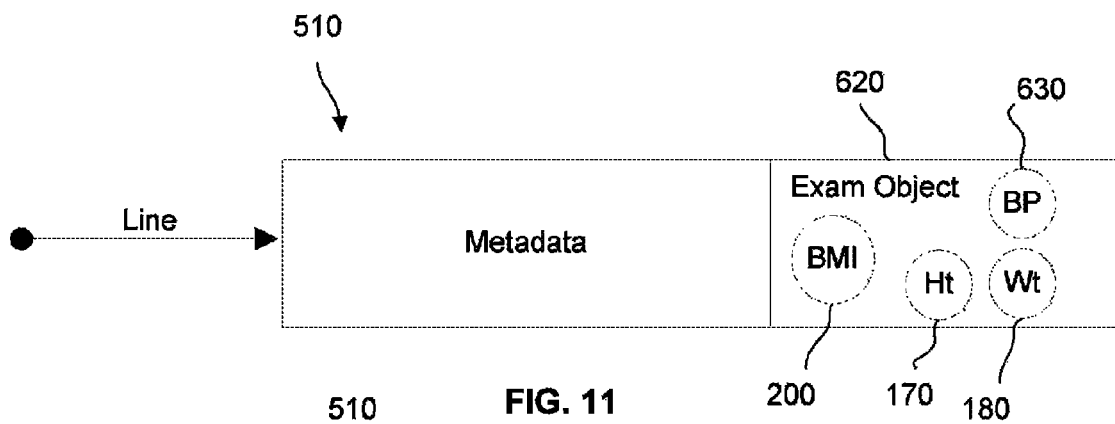

FIG. 11 illustrates a CCO 620 representing an examination that is part of a clinical encounter that holds a blood pressure granule 630, the height granule 170, the weight granule 180, and the BMI granule 200. The granules 170, 180, 200 and 630 are stored in the granule collection 310 in the base class 160, seen in FIG. 5.

Figure 12:
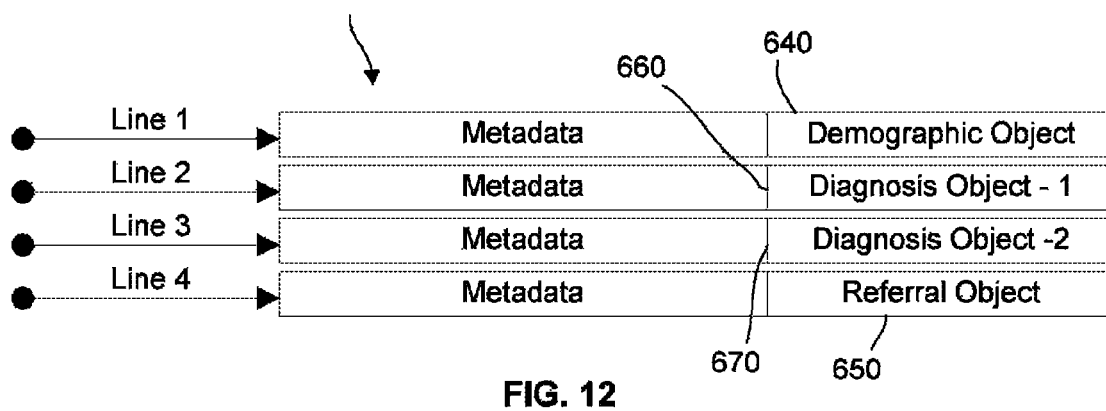

FIG. 12 illustrates an electronic medical record having a patient demographic CCO 640, a referral CCO 650, and two diagnoses CCOs 660 and 670. Each of the above CCOs 640, 650, 660 and 670 occupies their own row in the clinical table 510 seen in FIG. 9.

Figure 13:
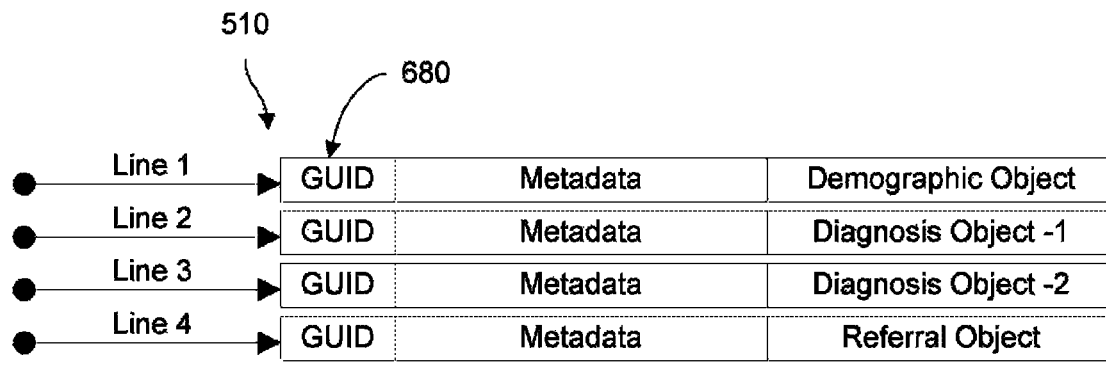

FIG. 13 illustrates how CCOs belonging to many different patients reside in the same clinical table 510. Patient GUID 680 is one of the metadata columns, which identifies each CCO object as belonging to a particular patient, such that a query using the patient GUID returns the entire patient's electronic medical records containing all objects tagged with the same GUID.

Persistent Storage—Referential Table

Referring again to FIGS. 1a and 9, the database server 130 in the datacenter 125 is delegated to hold the original footprint of the referential table 520, as the sole and authoritative source of all fixed or referential elements in the EMR information system 100. These fixed elements refer to codes and their descriptions contained in various coding systems, dictionaries, and indexes such as list of fees in billing systems, provider names in a provider index and so on.

The referential table 520 is easily updated and replicated as it is a solitary flat table. It is by design as flexible and extensible as the clinical table 150 described above. For example, new coding dictionaries and standards used in medical practice in any particular location or at any particular time may be easily changed or added without the need for modifying the EMR information system 100.

The proper functioning of the EMR information system 100 requires continuous access to these fixed elements in the referential table 520 whether they are accessible remotely or locally. The preferred method is to access these fixed elements locally, for example from within the thick client application 115 on the client machine 120. This allows the EMR information system 100 to operate without a connection between the client machine 120 and the database server 130. This is achieved by replicating the referential table 520 from its original footprint to every system that needs access to it.

Changes within the referential table 520 are typically made at the datacenter 125, which represents the highest organizational level. Changes made to entries in any of the fixed element collections can then be reflected back to all systems that depend on it for current and up to date information. Just as DNA, present in each cell of the human body, holds an entire copy of the human genetic code, so does each instance of the EMR information system 100 application hold a copy of the referential table 520, which can be thought of as the 'genetic code' of EMR information system 100.

The thick client application 115 on a client machine 120, seen in FIG. 1b, can be thought of as a cell in the human body having a private copy of the referential table 520, or its DNA. This method lends itself easily to distributed processing of medical context, for which the EMR information system 100 is designed.

The update table 530 and the live table 540 comprise entries relating to the changes in the referential table 520 so that changes in each system can be resolved through the updating code within the EMR information system 100. This ensures that the referential table 520 remains identical in each and every system. In the present example the thick client application 115 polls the database server 130 independently for changes in the referential table 520. However it is possible that in other examples the database server 130 can push changes to the client machines 110 and 120.

The EMR information system 100 also has the capability of automatically polling some of the data sources for changes. Any such changes in the data source will automatically update, add or delete their associated or representative entries in the referential table 520. This enables the transparent handling of common situations in the heath care field, for example, new or discontinued drugs, new or retired providers, changes in providers' contact information, etc. This provides EMR information system 100 users with current and up to date referential, or fixed, information.

The thick client application 115 on the client machine 120 can continue to function based on its copy of the referential table 520 stored in a local database alongside the thick client application 115. This is advantageous during situations that require either a disconnected state, or when connected systems experience a loss of connection to the datacenter 125 or other dependent servers. While updating cannot occur during a disconnected state, updating occurs automatically upon reconnection. Resolution of entries in the referential table 520 is determined by the information recorded in the update table 530 and the live table 540 described above.

The structure and the function of the referential table 520 is similar to that of the clinical table 510 used for storage of patient-specific clinical information. The clinical table 510 differs by having an additional column to deal with attributing CCO's to a specific clinical encounter.

Database Queries

Figure 14:
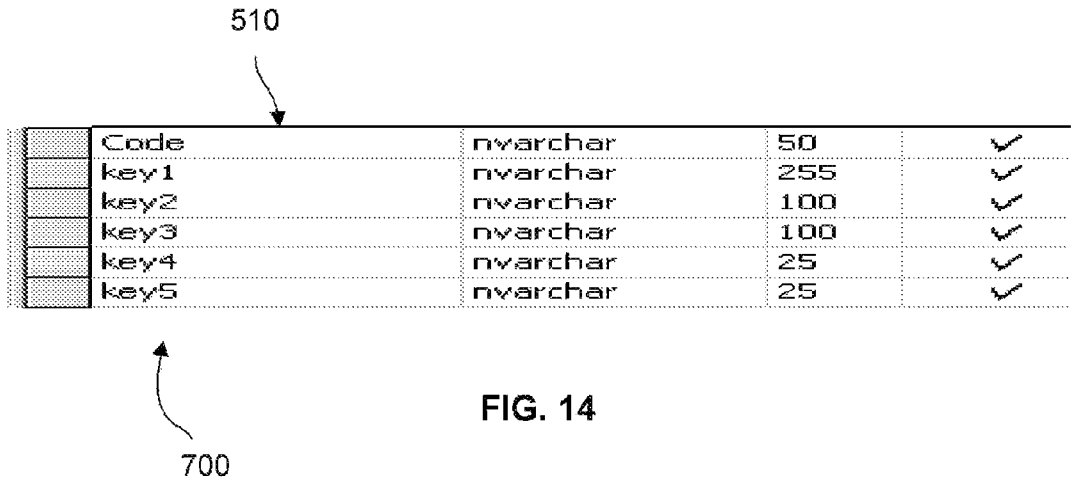
FIG. 14 is a simplified listing of column definitions of the clinical table of FIG. 9.

Referring to FIG. 14, queries on the clinical table 510 are now discussed. The EMR information system 100 utilizes citation key fields indicated generally by reference numeral 700, which are metadata columns within the clinical table 510. The keys 700 which are generated are chosen from the content of the CCO 340 requiring exposure to querying.

For example, a demographic CCO may expose the surname, and a diagnosis CCO may expose the ICD-9 diagnostic code. A referral CCO may expose the provider number of the physician receiving the referral. The clinical table 510 includes six citation key fields 700. However, this is extensible if necessary.

As mentioned above, the granular layer is embedded within the CCOs 340 so that deprecation is inherent throughout the entire clinical table 510. The granular layer can be sorted via a combination of direct mapping rules, or by inference through recognizing patterns in the granular layer.

Referring now to FIGS. 1b, 2, 9 and 21, a contextual encounter is described. A contextual encounter of a patient in a medical facility involves a clinician collecting current clinical information related to the patient, retrieving historical clinical information of the same clinical category and relevancy, and presenting the current and the historical contextual clinical information to the clinician.

The clinician enters clinical information related to the patient in step 875 of the thick client application 115 of the EMR information system 100. The clinical information is parsed by the thick client application 115 and at least one new clinical category object and corresponding new at least one granule object is created representative of the clinical information in step 880. The new clinical category objects and the new granule objects are stored in the clinical table 510.

Considering now one of the new granule objects, a recognition algorithm of the thick client application 115 searches the clinical table 510 for all historical granule objects in the patients electronic medical record of the same fundamental type of clinical information as the new granule object in step 885. The thick client application 115 performs an analysis on the new granule object and the historical granule objects and generates an opinion, or a diagnosis in step 890. The current and the historical granule objects are dynamically displayed to the clinician in step 895, for example in a tabular or graphical format, thereby showing any trend that may exist. The patient encounter is persisted in the clinical table 510 as an encounter clinical category object, and has associated with it a context encounter.

As a practical example, the clinician types into the thick client application 115 the textual string "BP 120/80" representing the blood pressure of the patient. The thick client application 115 creates a blood pressure granule object holding the value "120/80". Simultaneously, the thick client application 115 obtains a collection of all previously persisted historical blood pressure granule objects in the patient's electronic medical record within the clinical table 510. A graphical view showing the trend in blood pressure of the patient is presented to the clinician based on the new and historical blood pressure granule objects. Next, the clinician may enter a weight into the thick client application 115. The context is now changed, and the thick client application 115 responds in the manner presented above and displays historical contextual weight information. The enforced consistency of recordations of the clinical observations into granule objects is the foundation for such behavior.

Versioning

Figure 15:
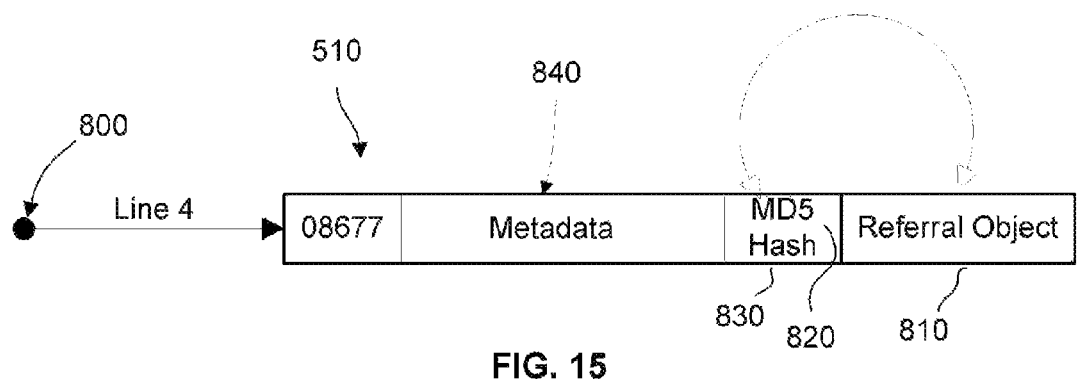
FIGS. 15 and 16 are block diagram views of rows of the clinical table of FIG. 9 illustrating versioning of electronic medical records.
Figure 16:
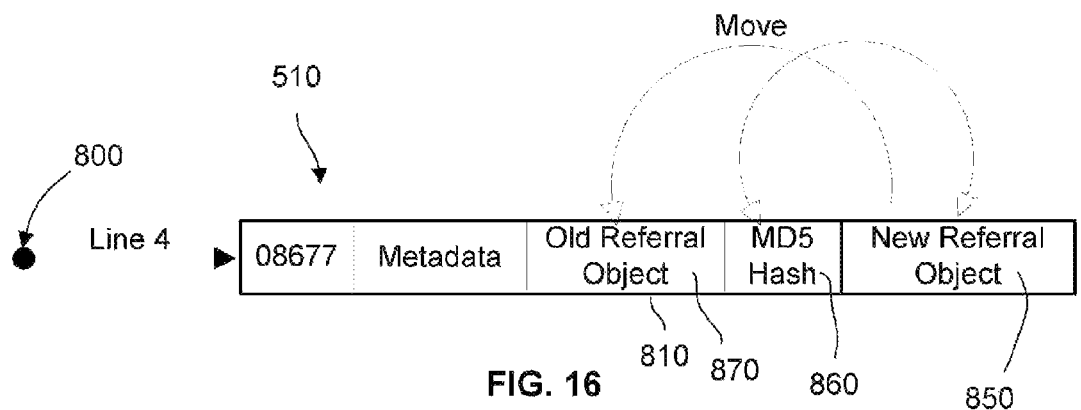

Referring now to FIGS. 15 and 16, the versioning process is now discussed. FIG. 15 illustrates a row 800 in the clinical table 510 which includes a referral CCO 810. The versioning process works by creating and maintaining an MD5 hash 820, which is stored in a DATA_HASH column 830 within metadata section of columns indicated generally by reference numeral 840. The MD5 hash represents the contents of the referral CCO 810.

During the normal use of the EMR information system 100 the referral CCO 810 may be edited or updated, creating a new referral object 850. Just before an update to the row 800 in the clinical table 510 occurs, a new MD5 hash 860 is calculated for the new referral CCO 850. If the new MD5 hash 860 is different than the old MD5 hash 820, the old referral CCO 810 is placed into a VERSIONSX metadata column 870. The VERSIONSX column 870 comprises a serialized object that stores all previous versions of the referral CCO object 850 along with the state of all of the metadata. Copying the row 810 of the clinical table 510 to another database has the effect of copying the current referral CCO 850 along with all of its previous versions. Since versions of a CCO reside within the same row of the clinical table 510 as the current CCO, relational database entries are not required.

Figure 17:
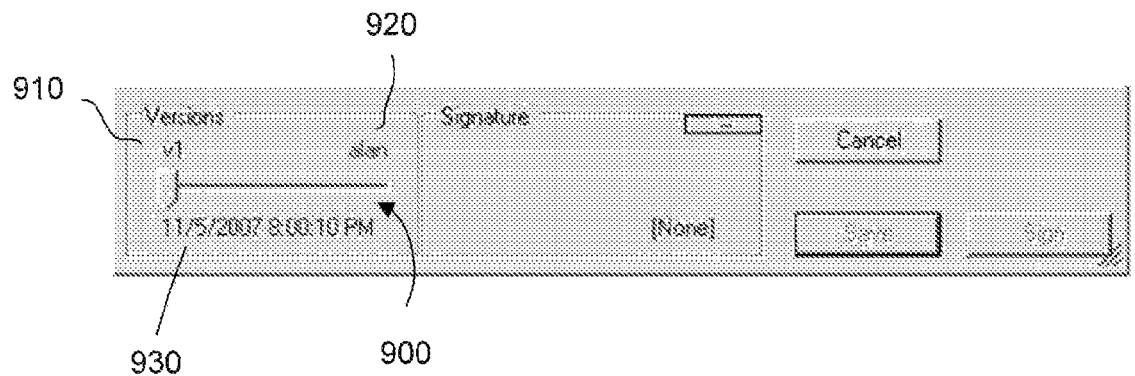
FIGS. 17, 18 and 19 are block diagram views of a slider control of the thick client application of FIG. 2.
Figure 18:
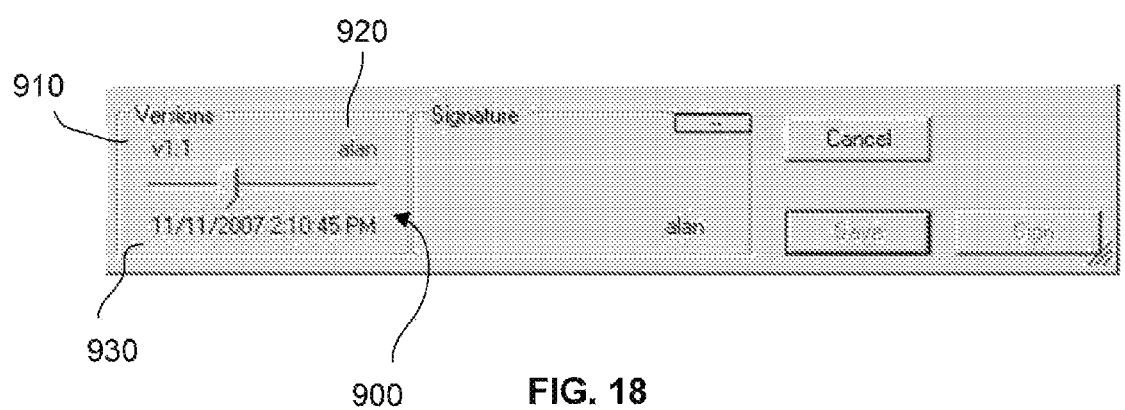
Figure 19:
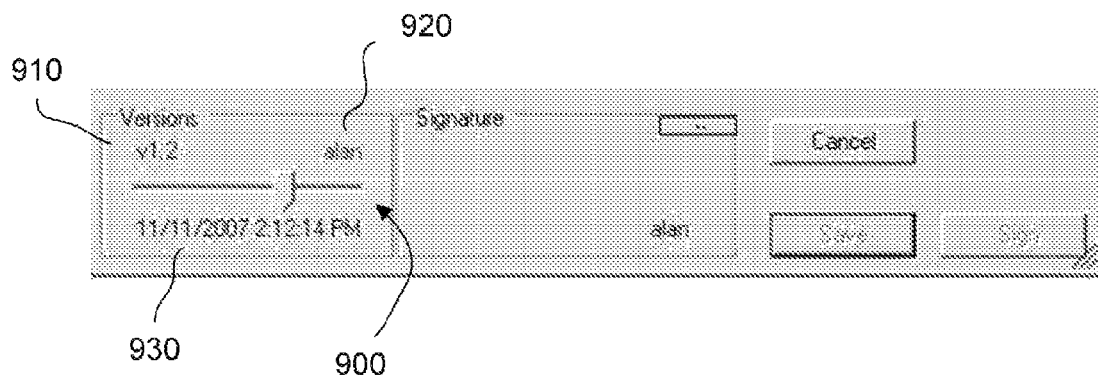
Figure 21:
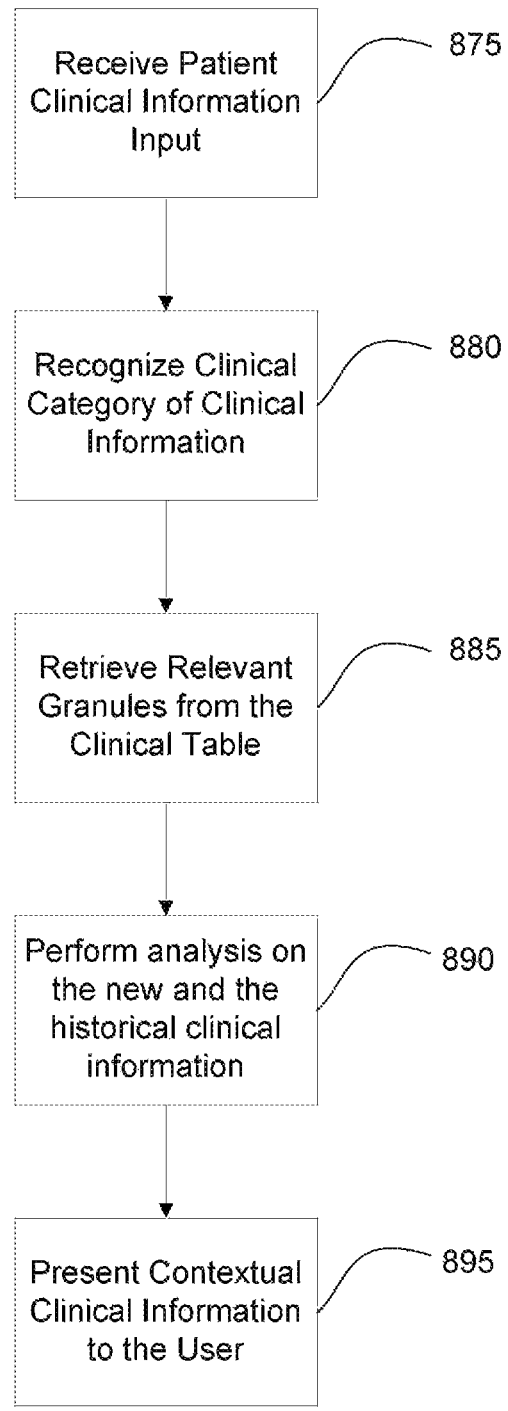
FIG. 21 is a flowchart diagram of a contextual encounter algorithm of the thick client application of FIG. 2.

Referring now to FIGS. 17, 18 and 19, the selection and playback of versions are discussed. The client machines 110 and 120 are used by the EMR information system 100 to present a graphical user interface to a user in order to view, modify and add EMR information. The graphical user interface visualizes the contents of the clinical category objects 340 to the user, and includes a slider control indicated generally by reference numeral 900 in FIGS. 17, 18 and 19.

Versions of the CCOs 340 are displayed interactively to the user by adjusting the slider control 900 such that the appropriate version is selected, as indicated by version selection text 910. The slider control 900 enables the instant visual playback of all the previous versions of clinical observations in chronological order. In addition, the slider control 900 presents information relating to the entity 920 responsible for the version as well as the detailed timestamp 930 of each version, such that the viewer can visually determine in real time what changes were made, by whom they were made, and when they were made.

Database Kernels

Referring again to FIG. 1b, the interface between the thick client application 115 and the flat file database 500 is now discussed. The thick client application 115 interfaces to the clinical table 510 and the referential table 520 through a clinical kernel 515 and a referential kernel 525 respectively. The operation of the two kernels 515 and 525 are similar in most respects.

The architecture of the EMR information system 100 constrains access to the data in the two tables 510 and 520 through the respective kernels 515 and 525. This enforcement allows for the application 115 to query and save data in a consistent manner and to enable the inherent features of the kernels 515 and 525 to be transparent and separate to the user interface. The functions that the kernels 515 and 525 provide are described next.

The kernels 515 and 525 provide querying functions in order to return the entire medical record of a patient. The patient's record is obtained by querying the GUID in the patient GUID column of the clinical table 510, as shown in FIG. 13 for example. The query returns all the CCO's in persistent storage for the particular patient.

The kernels 515 and 525 track users, organizations and the authoring of each CCO. Each CCO is stored with metadata as previously described. The metadata includes the above information based on the user who logged into EMR information system 100.

The kernels 515 and 525 provide functions to handle citation keys of each CCO 340. As CCO's are stored as a serialized binary field, they are not exposed to querying in the clinical table 510. The citation keys 700 shown in FIG. 14 are created to expose certain parts of a CCO into the 'key' columns so they can be subsequently queried.

The kernels 515 and 525 provide functions to save CCO's 340 to either the clinical table 510 or the referential table 520. The kernels physically save the data into the database with the assistance of a 3rd party persistent storage class.

The kernels 515 and 525 provide functions to direct the storage to a particular server. The user is not necessarily aware where the data is stored. The kernels 515 and 525 are able to detect and maintain the location of the persistent storage depending on circumstances, particularly with that of disconnected states.

The kernels 515 and 525 detect whether the user viewing the CCO has made changes to it. With appropriate permissions, the user is able to make changes to the fields and granules of a CCO. The kernels 515 and 525 are able to detect any changes made within the CCO.

The kernels 515 and 525 provide functions to determine whether versioning of the CCO is required. In conjunction with detection, versions reside within the same row but in a separate CCO.

The kernels 515 and 525 provide functions to handle the versioning process. For example, functions to store a versioned CCO into the same row as the current CCO.

The kernels 515 and 525 provide functions to serve versioned CCO's for playback to the user. The kernels provide access to all the previous versions of a CCO, such that the user can examine them through the unique playback method.

The kernels 515 and 525 provide functions to update and resolve CCO's between applications, i.e. the ability to resolve changes made to one CCO and to update its replicas.

The kernels 515 and 525 provide functions to animate some interface primitives like buttons, e.g. to animate buttons with colors to indicate the actions taken by the kernel.

The kernels 515 and 525 provide functions to secure the CCO by encrypting it.

While preferred embodiments of the present invention have been described, it is to be understood that the embodiments described are illustrative only and the scope of the invention is to be defined solely by the appended claims when accorded a full range of equivalence, many variations and modifications naturally occurring to those of skill in the art from a perusal hereof. As is readily apparent the system and method of the present invention is advantageous in several aspects.

What is claimed is:

1. A non-transitory memory for storing health information for access by an application program executed on a data processor or data processing system, the non-transitory memory comprising:
   a data structure stored in the memory, the data structure including health information resident in a flat file database;
   a plurality of granule information data structures, each of the granule information data structures having a collection of generic attributes and a global unique identifier attribute;
   a plurality of clinical observations, each of the clinical observations including a collection of the granule information data structures, each of the clinical observations having a collection of clinical attributes, and each of the clinical observations being stored as a single database row entry with the global unique identifier attribute in a metadata column;
   a plurality of clinical information data structures, each of the clinical information data structures including a base information data structure and a clinical category information structure, each said base information data structure including the collection of granule information data structures which are included in at least one of the clinical observations, and each said clinical category information data structure mapping the clinical attributes of the said at least one of the clinical observations to the generic attributes of the granule information data structures included in said at least one of the clinical observations; and
   an attribute database in the base information database structure of each of the clinical information data structures to allow new generic attributes to be added, wherein the granule information data structures are agnostic of the clinical observations and new said granule information data structures inherit the base information data structures of the clinical information data structures from which the new granule information data structures are created or derived, thereby allowing new said generic attributes to be added to the new granule information data structures without altering an existing architecture of the flat file database.

2. A computer data processor comprising a non-transitory memory for storing health information for access by an application program executed on the computer data processor, the non-transitory memory including:
   a data structure stored in the memory, the data structure including health information resident in a flat file database;
   a plurality of granule information data structures, each of the granule information data structures having a collection of generic attributes and a global unique identifier attribute;
   a plurality of clinical observations, each of the clinical observations including a collection of the granule information data structures, each of the clinical observations having a collection of clinical attributes, and each of the clinical observations being stored as a single database row entry with the global unique identifier attribute in a metadata column;
   a plurality of clinical information data structures, each of the clinical information data structures including a base information data structure and a clinical category information structure, each said base information data structure including the collection of granule information data structures which are included in at least one of the clinical observations, and each said clinical category information data structure mapping the clinical attributes of the said at least one of the clinical observations to the generic attributes of the granule information data structures included in said at least one of the clinical observations; and
   an attribute database in the base information database structure of each of the clinical information data structures to allow new generic attributes to be added, wherein the granule information data structures are agnostic of the clinical observations and new said granule information data structures inherit the base information data structures of the clinical information data structures from which the new granule information data structures are created or derived, thereby allowing new said generic attributes to be added to the new granule information data structures without altering an existing architecture of the flat file database.

3. A computer data processing system comprising a non-transitory memory for storing health information for access by an application program executed on a data processor of the computer data processing system, the non-transitory memory including:
   a data structure stored in the memory, the data structure including health information resident in a flat file database;
   a plurality of granule information data structures, each of the granule information data structures having a collection of generic attributes and a global unique identifier attribute;
   a plurality of clinical observations, each of the clinical observations including a collection of the granule information data structures, each of the clinical observations having a collection of clinical attributes, and each of the clinical observations being stored as a single database row entry with the global unique identifier attribute in a metadata column;
   a plurality of clinical information data structures, each of the clinical information data structures including a base information data structure and a clinical category information structure, each said base information data structure including the collection of granule information data structures which are included in at least one of the clinical observations, and each said clinical category information data structure mapping the clinical attributes of the said at least one of the clinical observations to the generic attributes of the granule information data structures included in said at least one of the clinical observations; and an attribute database in the base information database structure of each of the clinical information data structures to allow new generic attributes to be added, wherein the granule information data structures are agnostic of the clinical observations and new said granule information data structures inherit the base information data structures of the clinical information data structures from which the new granule information data structures are created or derived, thereby allowing new said generic attributes to be added to the new granule information data structures without altering an existing architecture of the flat file database.

* * * * *